United States Patent
Wong

(10) Patent No.: US 9,168,226 B1
(45) Date of Patent: Oct. 27, 2015

(54) INJECTABLE PARTICLE

(71) Applicant: David Wong, Milpitas, CA (US)

(72) Inventor: David Wong, Milpitas, CA (US)

(73) Assignee: David Wong, Milpitas, CA (US)

( * ) Notice: Subject to any disclaimer, the term of this patent is extended or adjusted under 35 U.S.C. 154(b) by 0 days.

(21) Appl. No.: 14/821,585

(22) Filed: Aug. 7, 2015

(51) Int. Cl.
  *A61K 31/497* (2006.01)
  *A61K 31/44* (2006.01)
  *A61K 9/14* (2006.01)
  *A61K 9/16* (2006.01)

(52) U.S. Cl.
  CPC .. *A61K 9/14* (2013.01); *A61K 31/44* (2013.01)

(58) Field of Classification Search
  None
  See application file for complete search history.

(56) References Cited

U.S. PATENT DOCUMENTS

| 2009/0209496 | A1 | 8/2009 | Chaplin | |
|---|---|---|---|---|
| 2015/0110871 | A1* | 4/2015 | Wong | A61K 9/0065 |
| | | | | 424/469 |
| 2015/0133464 | A1* | 5/2015 | Wong | A61K 9/1611 |
| | | | | 514/252.19 |
| 2015/0224060 | A1* | 8/2015 | Wong | A61K 9/5026 |
| | | | | 424/469 |

FOREIGN PATENT DOCUMENTS

| WO | WO/2010/067374 | 6/2010 |
| WO | WO/2010/139979 | 5/2011 |
| WO | WO/2010/139981 | 5/2011 |

OTHER PUBLICATIONS

SciFinder search results for dasatinib acetate; downloaded Aug. 26, 2015.*

* cited by examiner

*Primary Examiner* — Jeffrey T Palenik

(57) ABSTRACT

The present invention provides an injectable particle comprising dasatinib acetate and a hyaluronic acid. The hyaluronic acid may be acetylated or sulfated. The particle is for the use of cancer therapy. The injectable particle may further comprises an acid, wherein the acid is dispersed evenly in the matrix of the injectable particle.

10 Claims, No Drawings

INJECTABLE PARTICLE

TECHNICAL FIELD

The present invention generally relates to an novel injectable particle composition comprising dasatinib acetate and further hyaluronic acid. The hyaluronic acid may be acetylated or sulfated. The particle is for the use of cancer therapy.

BACKGROUND OF THE INVENTION

Dasatinib is a kinase inhibitor; it works by blocking the action of an abnormal protein that signals cancer cells to multiply. Dasatinib is used to treat a certain type of chronic myeloid leukemia and a certain type of acute lymphoblastic leukemia in people who can no longer benefit from other medications for leukemia or who cannot take these medications because of side effects. However, Carlson, Robert, H, (Oncology Times, Volume 36, Issue 18, p 27, Sep. 25, 2014) found that dasatinib did not increase survival of patients suffered from advanced pancreatic cancer when combined with gemcitabine compared with gemcitabine alone.

Dansatinib exhibits pH dependent aqueous solubility (from 18.4 mg/ml at pH 2.6 to 0.008 mg/ml at pH 6.0). WO2010139981 A2 teaches processes for the preparation of dasatinib and to crystalline monohydrate and anhydrous polymorphic forms of dasatinib, WO2010139981 A2 also teach a method for preparing dasatinib acetate, but WO2010139981 A2 does not teach the use of dasatinib acetate.

BRIEF SUMMARY OF THE INVENTION

Accordingly, the present invention relates to an novel injectable particle composition comprising dasatnib acetate for treating cancers.

DETAILED DESCRIPTION OF THE INVENTION

Definitions

Singular forms included in the claims such as "a", "an" and "the" include the plural reference unless expressly stated or the context clearly indicates otherwise.

"Optional" or "optionally" means that the subsequently described circumstance may or may not occur, so that the description includes instances where the circumstance occurs and instances where it does not.

The term, injectable particles, refers to solid particles with an average size of about 5 nm to about 50,000 nm, and these solid particles are intended to be delivered via intravenous injection or other means for chemotherapy.

Hyaluronic acid (HA) is a polysaccharide composed of alternating molecules of N-acetyl glucosamine and D-glucuronic acid. It can be found within collagen throughout the body. HA sodium salt from *Streptococcus equi* is available at SIGMA-ALDRICH®. The preferred molecular weight of HA is slightly below 3,500 Da.

Chen G et al, Bioconjug Chem 1997 September-October, 8(5) 730-4 suggests that HA can be sulfated by a sulfur trioxide-pyridine complex to form sulfated HA. Barbucci R. et al, J. Thromb Thrombolysis, 1998 September; 6(2): 109-115, suggest sulfation of the —OH groups of HA to prepare different sHA derivatives.

U.S. Pat. No. 6,673,919 B2 describes a detailed method for the preparation of the acetylated HA (aHA). While, Carmela Saturnino et al, BioMed Research International; Volume 2014 (2014), also suggest a method for the preparation of aHA: (1) adding catalytic amount of 4-dimethylaminopyridine (DMAP) and an excess of acetic anhydride to a stirred cold solution of 500 mg sodium hyaluronate in 10 ml of toluene. (2) stirring the mixture at reflux, under nitrogen, for 24 hours and then concentrate the mixture under reduced pressure, (3) purifying the solid residue by silica gel chromatography using dichloromethane and methanol (in a ratio of 9:1) as eluent, and then obtaining the pure compound as white solid.

The present invention provides an novel injectable particle composition comprising dasatinib acetate and further hyaluronic acid. The hyaluronic acid may be acetylated or sulfated. The particle is for the use of cancer therapy. Consequently, the particle may have one or more of the following characteristics: (1) the matrix comprising dosatinib acetate, (2) the matrix also comprising hyaluronic acid, the hyaluronic acid may be acetylated or sulfated, and (3) the particle size is about 5 nm to about 50,000 nm, and (4) the particle is for the use of cancer therapy.

The injectable particles are prepared by the following steps: (1) dissolving hyaluronic acid in an aqueous medium to form hyaluronic acid solution, (2) dispersing dasatinib acetate in the hyaluronic acid solution, and (3) spray-drying the dispersion of step 2 into injectable particles. For matrix comprising acetylated hyaluronic acid, hyaluronic acid is substituted by acetylated hyaluronic acid in the preparation. For matrix comprising sulfated hyaluronic acid, hyaluronic acid is substituted by sulfated hyaluronic acid. In certain conditions, acids are present in the aqueous medium of step 1. Nagavarma B V N et al, Asian Journal of Pharmaceutical and Clinical Research 2012, 5(3): 16-23, describe nanoprecipitation and solvent displacement method for preparing nanoparticles of water-soluble drugs in a water-miscible solvent. While, Do Hyung Kim et al, Nanoscale Research Letters 2012, 7:91, describes a preparation method of sorafenib nanoparticles by nanoprecipitation-dialysis. Further, Manisha Khemani et al, Annals of Biological Research, 2012, 3(9): 4414-4419, describes a method for preparing nanoparticles comprising doxorubicin HCl and PLGA. Kim et al, Int J Nanomedicine 2011, 6: 2621-2631 teaches a method for preparing nanoparticles comprising celecoxib and PLGA. Finally, U.S. Pat. No. 8,303,992 and U.S. Pat. No. 5,674,531 teach a method of spray-drying dispersions to form particles, and U.S. Pat. No. 7,901,711 teaches a method of freeze-drying of a mixture to form particles. However, alternative nanoparticle preparation methods, such as electrospray, critical fluid etc., can be used as substitutes for the method described above.

Accordingly, the present invention provides an injectable particle comprising dasatinib acetate and further hyaluronic acid. The hyaluronic acid may be acetylated or sulfated. The particle is for the use of cancer therapy. The injectable particle may further comprises an acid, wherein the acid is dispersed evenly in the matrix of the injectable particle.

In one embodiment, the injectable particle comprises dasatinib acetate, hyaluronic acid and a surfactant. In one aspect, the hyaluronic acid is acetylated. In another aspect, the hyaluronic acid is sulfated.

In another embodiment, the injectable particle comprises dasatinib acetate, hyaluronic acid and an organic acid. In one aspect, the hyaluronic acid is acetylated. In another aspect, the hyaluronic acid is sulfated. The preferred organic acids are rosin acids.

In a further embodiment, the injectable particle comprises dasatinib acetate, hyaluronic acid, a surfactant and an organic acid. In one aspect, the hyaluronic acid is acetylated. In another aspect, the hyaluronic acid is sulfated. The preferred organic acids sodium lauryl sulfate and polysorbate 80.

In a further embodiment, the injectable particle comprises dasatinib acetate, hyaluronic acid, a surfactant, an organic acid. In one aspect, the hyaluronic acid is acetylated. In another aspect, the hyaluronic acid is sulfated.

In all embodiments, the injectable particle optionally comprises hyaluronidase and dasatnib, wherein hyaluronidases are a family of enzymes that degrade hyaluronic acid. The injectable particle may be used for treating cancers including a certain type of pancreatic cancers.

EXAMPLES OF INVENTION

The foregoing examples are illustrative embodiments of the invention and are merely exemplary. A person skilled in the art may make variations and modifications without deviating from the spirit and scope of the invention. All such modifications and variations are intended to be included within the scope of the invention.

Example 1

Hyaluronic acid is dissolved in an aqueous medium to form a hyaluronic acid solution. Dasatinib acetate is dispersed in the hyaluronic acid solution to form a dispersion. The dispersion is then spray-dried to form the injectable particles.

Example 2

Acetylated hyaluronic acid (aHA) is dissolved in an aqueous medium to form aHA solution. Dasatinib acetate is dispersed in the aHA solution to form a dispersion. The dispersion is then spray-dried to form the injectable particles.

Example 3

Sulfated hyaluronic acid (sHA) is dissolved in an aqueous medium to form a sHA solution. Dasatinib acetate is dispersed in the sHA solution to form a dispersion. The dispersion is then spray-dried to form the injectable particles.

Example 4

Hyaluronic acid (HA) and rosin acids (RA) are dissolved in an aqueous medium to form a HA/RA solution. Dasatinib acetate is dispersed in the HA/RA solution to form a dispersion. The dispersion is then spray-dried to form the injectable particles.

Example 5

Acetylated hyaluronic acid (aHA) and rosin acids (RA) are dissolved in an aqueous medium to form aHA/RA solution. Dasatinib acetate is dispersed in the aHA/RA solution to form a dispersion. The dispersion is then spray-dried to form the injectable particles.

Example 6

Sulfated hyaluronic acid (sHA) and rosin acids (RA) are dissolved in an aqueous medium to form a sHA/RA solution. Dasatinib acetate is dispersed in the sHA/RA solution to form a dispersion. The dispersion is then spray-dried to form the injectable particles.

Example 7

Hyaluronic acid (HA) and polysorbate 80 (p80) are dissolved in an aqueous medium to form a HA/p80 solution. Dasatinib acetate is dispersed in the HA/p80 solution to form a dispersion. The dispersion is then spray-dried to form the injectable particles.

Example 8

Acetylated hyaluronic acid (aHA) and sodium lauryl sulfate (SLS) are dissolved in an aqueous medium to form aHA/SLS solution. Dasatinib acetate is dispersed in the aHA/SLS solution to form a dispersion. The dispersion is then spray-dried to form the injectable particles.

Example 9

Sulfated hyaluronic acid (sHA) and sodium lauryl sulfate (SLS) are dissolved in an aqueous medium to form a sHA/SLS solution. Dasatinib acetate is dispersed in the sHA/SLS solution to form a dispersion. The dispersion is then spray-dried to form the injectable particles.

Example 10

Hyaluronic acid (HA), rosin acids (RA) and sodium lauryl sulfate (SLS) are dissolved in an aqueous medium to form a HA/RA/SLS solution. Dasatinib acetate is dispersed in the HA/RA/SLS solution to form a dispersion. The dispersion is then spray-dried to form the injectable particles.

Example 11

Acetylated hyaluronic acid (aHA), rosin acids (RA) and sodium lauryl sulfate (SLS) are dissolved in an aqueous medium to form aHA/RA/SLS solution. Dasatinib acetate is dispersed in the aHA/RA/SLS solution to form a dispersion. The dispersion is then spray-dried to form the injectable particles.

Example 12

Sulfated hyaluronic acid (sHA), rosin acids (RA) and sodium lauryl sulfate (SLS) are dissolved in an aqueous medium to form a sHA/RA/SLS solution. Dasatinib acetate is dispersed in the sHA/RA/SLS solution to form a dispersion. The dispersion is then spray-dried to form the injectable particles.

Example 13

Hyaluronic acid and a hyaluronidase are dissolved in an aqueous medium to form a hyaluronic acid solution. Dasatinib acetate is dispersed in the hyaluronic acid solution to form a dispersion. The dispersion is then spray-dried to form the injectable particles.

Example 14

Acetylated hyaluronic acid (aHA) and a hyaluronidase are dissolved in an aqueous medium to form aHA solution. Dasatinib acetate is dispersed in the aHA solution to form a dispersion. The dispersion is then spray-dried to form the injectable particles.

Example 15

Sulfated hyaluronic acid (sHA) and a hyaluronidase are dissolved in an aqueous medium to form a sHA solution.

Dasatinib acetate is dispersed in the sHA solution to form a dispersion. The dispersion is then spray-dried to form the injectable particles.

Example 16

Hyaluronic acid (HA), a hyaluronidase and rosin acids (RA) are dissolved in an aqueous medium to form a HA/RA solution. Dasatinib acetate is dispersed in the HA/RA solution to form a dispersion. The dispersion is then spray-dried to form the injectable particles.

Example 17

Acetylated hyaluronic acid (aHA), a hyaluronidase and rosin acids (RA) are dissolved in an aqueous medium to form aHA/RA solution. Dasatinib acetate is dispersed in the aHA/RA solution to form a dispersion. The dispersion is then spray-dried to form the injectable particles.

Example 18

Sulfated hyaluronic acid (sHA), a hyaluronidase and rosin acids (RA) are dissolved in an aqueous medium to form a sHA/RA solution. Dasatinib acetate is dispersed in the sHA/RA solution to form a dispersion. The dispersion is then spray-dried to form the injectable particles.

Example 19

Hyaluronic acid (HA), a hyaluronidase and sodium lauryl sulfate (SLS) are dissolved in an aqueous medium to form a HA/SLS solution. Dasatinib acetate is dispersed in the HA/SLS solution to form a dispersion. The dispersion is then spray-dried to form the injectable particles.

Example 20

Acetylated hyaluronic acid (aHA), a hyaluronidase and sodium lauryl sulfate (SLS) are dissolved in an aqueous medium to form aHA/SLS solution. Dasatinib acetate is dispersed in the aHA/SLS solution to form a dispersion. The dispersion is then spray-dried to form the injectable particles.

Example 21

Sulfated hyaluronic acid (sHA), a hyaluronidase and sodium lauryl sulfate (SLS) are dissolved in an aqueous medium to form a sHA/SLS solution. Dasatinib acetate is dispersed in the sHA/SLS solution to form a dispersion. The dispersion is then spray-dried to form the injectable particles.

Example 22

Hyaluronic acid (HA), rosin acids (RA), a hyaluronidase and sodium lauryl sulfate (SLS) are dissolved in an aqueous medium to form a HA/RA/SLS solution. Dasatinib acetate is dispersed in the HA/RA/SLS solution to form a dispersion. The dispersion is then spray-dried to form the injectable particles.

Example 23

Acetylated hyaluronic acid (aHA), a hyaluronidase, rosin acids (RA) and sodium lauryl sulfate (SLS) are dissolved in an aqueous medium to form aHA/RA/SLS solution. Dasatinib acetate is dispersed in the aHA/RA/SLS solution to form a dispersion. The dispersion is then spray-dried to form the injectable particles.

Example 24

Sulfated hyaluronic acid (sHA), a hyaluronidase, rosin acids (RA) and sodium lauryl sulfate (SLS) are dissolved in an aqueous medium to form a sHA/RA/SLS solution. Dasatinib acetate is dispersed to form a dispersion. The dispersion is then spray-dried to form the injectable particles.

Example 25

Sulfated hyaluronic acid (sHA), a hyaluronidase, rosin acids (RA) and sodium lauryl sulfate (SLS) are dissolved in an aqueous medium to form a sHA/RA/SLS solution. Dasatinib acetate and dsatinib are dispersed to form a dispersion. The dispersion is then spray-dried to form the injectable particles.

Example 26

Acetylated hyaluronic acid (aHA), a hyaluronidase, rosin acids and sodium lauryl sulfate (SLS) are dissolved in an aqueous medium to form aHA/SLS solution. Dasatinib acetate and dasatinib are dispersed in the aHA/SLS solution to form a dispersion. The dispersion is then spray-dried to form the injectable particles.

Example 27

Acetylated hyaluronic acid (aHA), a hyaluronidase, rosin acids and polysorbate 80 (p80) are dissolved in an aqueous medium to form aHA/p80 solution. Dasatinib acetate and dasatinib are dispersed in the aHA/p80 solution to form a dispersion. The dispersion is then spray-dried to form the injectable particles.

I claim:

1. An injectable particle comprising dasatinib acetate and hyaluronic acid.
2. The injectable particle according to claim 1, wherein the hyaluronic acid is acetylated.
3. The injectable particle according to claim 1, wherein the hyaluronic acid is sulfated.
4. The injectable particle according to claim 1 further comprising an acid, wherein the acid is dispersed evenly in the matrix of the injectable particle, and wherein the acid is rosin acids.
5. An injectable particle comprising dasatinib acetate, a hyaluronic acid and a surfactant, wherein the surfactant is selected from the group consisting of sodium lauryl sulfate and polysorbate 80.
6. The injectable particle according to claim 5, wherein the hyaluronic acid is acetylated.
7. The injectable particle according to claim 5, wherein the hyaluronic acid is sulfated.
8. The injectable particle according to claim 5 further comprising an acid, wherein the acid is dispersed evenly in the matrix of the injectable particle, and wherein the acid is rosin acids.
9. An injectable particle comprising dasatinib acetate, acetylated hyaluronic acid, polysorbate 80 and rosin acids.
10. The injectable particle according to claim 9 optionally comprising hyaluronidase, wherein the injectable particle is for treating a certain type of pancreatic cancers, and wherein the injectable particle optionally comprises dasatinib.

* * * * *